(12) United States Patent
Górová et al.

(10) Patent No.: US 11,850,119 B2
(45) Date of Patent: Dec. 26, 2023

(54) HEARING SAFETY DEVICE

(71) Applicant: Honeywell International Inc., Charlotte, NC (US)

(72) Inventors: Simona Górová, Olšany u Prostějova (CZ); Veronika Růžičková, Lukov u Zlína (CZ); Karolína Hájková, Vyškov (CZ); Monika Leskovská, Sudoměřice (CZ); Tanguy Prévot, Nebovidy u Brna (CZ)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 17/466,971

(22) Filed: Sep. 3, 2021

(65) Prior Publication Data

US 2023/0072510 A1    Mar. 9, 2023

(51) Int. Cl.
*A61F 11/14* (2006.01)
*H04R 1/10* (2006.01)
*A42B 3/16* (2006.01)

(52) U.S. Cl.
CPC ............ *A61F 11/14* (2013.01); *H04R 1/1008* (2013.01); *H04R 1/1083* (2013.01); *A42B 3/166* (2013.01); *A61F 11/145* (2022.01); *A61F 2250/0008* (2013.01); *H04R 2400/01* (2013.01); *H04R 2410/01* (2013.01)

(58) Field of Classification Search
CPC ........ A61F 11/08; A61F 11/14; A61F 11/145; A61F 2250/0008; H04R 1/008; H04R 1/1083; H04R 2400/01; H04R 2410/01; A42B 3/166
See application file for complete search history.

(56) References Cited

U.S. PATENT DOCUMENTS

| 4,023,642 | A | * | 5/1977 | Korn | A61F 11/14 181/129 |
|---|---|---|---|---|---|
| 4,060,701 | A | * | 11/1977 | Epley | H04R 29/00 73/584 |
| 2007/0269072 | A1 | * | 11/2007 | Pfanner | A61F 11/12 381/379 |
| 2008/0025524 | A1 | * | 1/2008 | Vaudrey | A61F 11/14 381/72 |
| 2008/0263749 | A1 | * | 10/2008 | Leong | A61F 11/14 2/209 |
| 2010/0074451 | A1 | * | 3/2010 | Usher | H04R 1/1091 381/58 |

(Continued)

*Primary Examiner* — Carolyn R Edwards
*Assistant Examiner* — Kuassi Ganmavo
(74) *Attorney, Agent, or Firm* — Alston & Bird LLP

(57) ABSTRACT

Devices, methods, and computer program products are provided herein for hearing safety. An example hearing safety device configured to be worn by a user includes an earmuff body that defines an interior cavity configured to receive the user's ear therein when worn by the user and an exterior surface opposite the interior cavity. The hearing safety device includes an ear lid attached to a surface of the interior cavity. The ear lid projects into the interior cavity from the surface of the interior cavity and defines a sealing surface configured to substantially seal an ear canal of the user's ear when the hearing safety device is worn by the user. The hearing safety device also includes an adjustment mechanism operably attached to the ear lid and configured to move the ear lid relative the interior cavity of the earmuff body.

20 Claims, 7 Drawing Sheets

(56) References Cited

U.S. PATENT DOCUMENTS

| | | | | |
|---|---|---|---|---|
| 2015/0010158 A1* | 1/2015 | Broadley | ................ | A61F 11/14 |
| | | | | 381/58 |
| 2016/0058619 A1* | 3/2016 | Goldfarb | ................. | A61F 11/10 |
| | | | | 128/864 |
| 2017/0208380 A1* | 7/2017 | Slater | ................... | H04R 1/1083 |
| 2018/0262825 A1* | 9/2018 | Boyer | .................... | H04R 1/105 |
| 2019/0318719 A1* | 10/2019 | Copt | ................ | G10K 11/17857 |
| 2022/0362059 A1* | 11/2022 | Henry | ..................... | A61F 11/14 |

\* cited by examiner

HEARING SAFETY DEVICE

TECHNOLOGICAL FIELD

Example embodiments of the present disclosure relate generally to sound attenuation and, more particularly, to devices and methods for improved hearing safety.

BACKGROUND

Workers in a variety of environments, such as airports, drilling/mining locations, manufacturing facilities, and the like, may be exposed to consistent and/or intermittent sound at dangerous intensities or levels. Without proper protective equipment, exposure to this sound may result in damage to a worker's hearing. The inventors have identified numerous deficiencies with these existing technologies in the field of hearing protection, the remedies for which are the subject of the embodiments described herein.

BRIEF SUMMARY

Devices, methods, systems, and associated computer program products are provided for improved hearing protection. An example hearing safety device configured to be worn by a user may include an earmuff body that defines an interior cavity configured to receive the user's ear therein when worn by the user and an exterior surface opposite the interior cavity. The device may further include an ear lid attached to a surface of the interior cavity that projects into the interior cavity from the surface of the interior cavity. The ear lid may define a sealing surface configured to substantially seal an ear canal of the user's ear when the hearing safety device is worn by the user. The device may further include an adjustment mechanism operably attached to the ear lid and configured to move the ear lid relative the interior cavity of the earmuff body.

In some embodiments, the sealing surface may be further configured to prevent entry of the ear lid into the ear canal of the user when the hearing safety device is worn by the user.

In some embodiments, the sealing surface may be further dimensioned to cover the ear canal of the user without entering the ear canal.

In some embodiments, the adjustment mechanism may include a spring configured to urge the ear lid toward the ear canal of the user when the hearing safety device is worn by the user.

In some further embodiments, the adjustment mechanism may further include an adjustment input device operably attached to the spring and configured to modify the tension in the spring so as to modify the force applied to the ear lid and the user.

In some still further embodiments, the adjustment input device may include a rotary knob defined by the exterior surface of the earmuff body.

In some embodiments, the hearing safety device may further include a sealing membrane disposed at a juncture between the interior cavity and the exterior surface. The sealing membrane may be configured to substantially seal the interior cavity from an external environment in an instance in which the hearing safety device is worn by the user.

In some embodiments, the hearing safety device may further include a microphone attached to the exterior surface of the earmuff body. The microphone may be configured to be disposed proximate the user's mouth in an instance in which the hearing safety device is worn by the user.

In some embodiments, the hearing safety device may further include a first sensor operably coupled with the interior cavity and configured to generate first sensor data indicative of a sound intensity within the interior cavity.

In some further embodiments, the hearing safety device may include a second sensor operably coupled with an exterior environment of the hearing safety device and configured to generate second sensor data indicative of a sound intensity of the exterior environment.

In some still further embodiments, the hearing safety device may include a controller operably coupled with the first sensor and the second sensor. The controller may be configured to receive the first sensor data from the first sensor, receive the second sensor data from the second sensor, determine a sound intensity difference between the sound intensity within the interior cavity and the sound intensity of the exterior environment, and cause, via the adjustment mechanism, the ear lid to move relative the interior cavity of the earmuff body based upon the determined sound level difference.

In some further embodiments, the controller may be further configured to compare the determined sound intensity difference with a safety threshold and cause, via the adjustment mechanism, the ear lid to move in an instance in which the determined sound intensity difference satisfies the safety threshold.

In some embodiments, the hearing safety device may further include a speaker operably coupled with the interior cavity of the earmuff body and configured to output sound.

In some further embodiments, the hearing safety device may include a controller operably coupled with the speaker. The controller may be configured to receive a sound transmission configured for output by the speaker, and cause, via the adjustment mechanism, the ear lid to move relative the interior cavity of the earmuff body in response to the sound transmission.

In some still further embodiments, the sound transmission may define a time period during which the sound transmission is output by the speaker, In such an embodiment, the controller may be further configured to move, via the adjustment mechanism, the ear lid from a first position at which the ear canal of the user is substantially sealed to a second position at which the ear canal of the user is open and move, via the adjustment mechanism, the ear lid from the second position to the first position at the conclusion of the time period.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings. The components illustrated in the figures may or may not be present in certain embodiments described herein. Some embodiments may include fewer (or more) components than those shown in the figures.

DETAILED DESCRIPTION

Figure 1A:
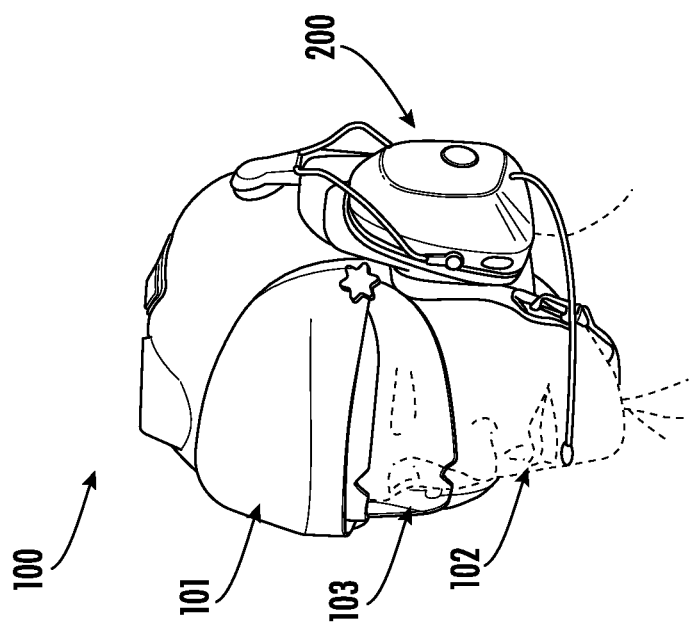
FIGS. 1A-1B illustrate an example personal protective equipment (PPE) assembly for implementing an example hearing safety device of the present disclosure in accordance with some example embodiments described herein.

Some embodiments of the present disclosure will now be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout. As used herein, terms such as "front," "rear," "top," etc. are used for explanatory purposes in the examples provided below to describe the relative position of certain components or portions of components. Furthermore, as would be evident to one of ordinary skill in the art in light of the present disclosure, the terms "substantially" and "approximately" indicate that the referenced element or associated description is accurate to within applicable engineering tolerances.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

As used herein, the phrases "in one embodiment," "according to one embodiment," "in some embodiments," and the like generally refer to the fact that the particular feature, structure, or characteristic following the phrase may be included in at least one embodiment of the present disclosure. Thus, the particular feature, structure, or characteristic may be included in more than one embodiment of the present disclosure such that these phrases do not necessarily refer to the same embodiment.

As used herein, the word "example" is used herein to mean "serving as an example, instance, or illustration." Any implementation described herein as "example" is not necessarily to be construed as preferred or advantageous over other implementations.

As used herein, the terms "data," "content," "information," "electronic information," "signal," "command," and similar terms may be used interchangeably to refer to data capable of being transmitted, received, and/or stored in accordance with embodiments of the present disclosure. Thus, use of any such terms should not be taken to limit the spirit or scope of embodiments of the present disclosure. Further, where a first device is described herein to receive data from a second device, it will be appreciated that the data may be received directly from the second device or may be received indirectly via one or more intermediary computing devices, such as, for example, one or more servers, relays, routers, network access points, base stations, hosts, and/or the like, sometimes referred to herein as a "network." Similarly, where a first device is described herein as sending data to a second device, it will be appreciated that the data may be sent directly to the second device or may be sent indirectly via one or more intermediary computing devices, such as, for example, one or more servers, remote servers, cloud-based servers (e.g., cloud utilities), relays, routers, network access points, base stations, hosts, and/or the like.

As used herein, the term "computer-readable medium" refers to non-transitory storage hardware, non-transitory storage device or non-transitory computer system memory that may be accessed by a computing device, a microcomputing device, a computational system or a module of a computational system to encode thereon computer-executable instructions or software programs. A non-transitory "computer-readable medium" may be accessed by a computational system or a module of a computational system to retrieve and/or execute the computer-executable instructions or software programs encoded on the medium. Exemplary non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM), and the like.

Overview

Figure 1B:
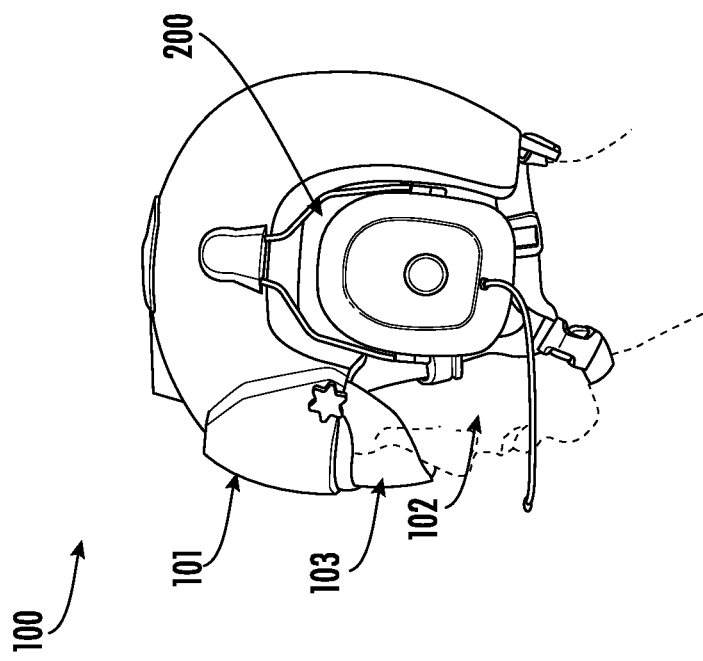

With reference to FIGS. 1A-1B, an PPE assembly 100 is illustrated with which an example hearing safety device 200 of the present disclosure may be implemented. As described above, various environments, such as airports, drilling and mining locations, manufacturing facilities, and the like, may expose workers at these locations to intense noise or sound levels. In order to attenuate this exposure, PPE assemblies such as those illustrated in FIGS. 1A-1B may be worn by a user 102 (e.g., a worker, operator, etc.). For example, a user 102 may wear a helmet 101 that is configured to shield a user's head from impact and/or an eye shield 103 configured to prevent particulate matter from entering the user's eyes. Furthermore, an example PPE assembly 100 may also provide hearing safety or protection such as via the hearing safety devices 200 of the present disclosure as described hereafter. The present disclosure contemplates that the devices described hereafter may be applicable to PPE assemblies 100 and industries or environments of any type and may further be in compliance with applicable hearing related safety regulations, rules, or the like.

Traditional attempts to attenuate intense sound exposure have often relied upon safety earmuffs or headphones that dampen the sound waves (e.g., reduce the energy of the sound waves propagating through the medium of the earmuffs or headphones). In many environments, however, these devices fail to provide sufficient sound attenuation to prevent hearing damage, such as in the oil and gas industry where large equipment, aircraft, and the like generate sound with intensities that greatly exceed the attenuation abilities of conventional safety earmuffs or headphones. As such, ear plugs or other similar devices that are inserted within a user's ear canal have been used in conjunction with these earmuffs or headphones in order to increase the attenuation offered by traditional hearing safety solutions. In practice, however, ear plugs are often misused by users in that they aren't properly secured at an appropriate location within a user's ear canal due to user error. Furthermore, the use of an ear plug secured within a user's ear canal is often uncomfortable to the user resulting in infrequent use.

Additionally, each of these traditional hearing protection solutions fail to provide for variability of sound wave attenuation during use. By way of example, in some environments, microphones and associated speakers may be used to allow a user to communicate with other users in the environment (e.g., transmitting or receiving commands from a control location or the like). The use of ear plugs within a user's ear canal often results in the inability for the user to properly receive sound transmission (e.g., the ear plug prevents the user from hearing commands provided via a speaker of a headset/headphones) or require the user to frequently remove and replace the ear plugs during communication. Furthermore, some environments provide a varying level or intensity of sound such that the associated level of required attenuation similarly varies. Traditional combinations of ear plugs with overlaid earmuffs or headphones fail to provide variable sound attenuation that is responsive to these changes in sound intensity within a user's work environment. Accordingly, the hearing safety devices 200 of the present disclosure described herein provide a solution to reduce or prevent hearing damage of users that is variable in sound attenuation, responsive to communication transmissions, and does not enter into the user's ear canal.

Hearing Safety Device

With reference to FIGS. 2A-5, an example hearing safety device 200 (e.g., device 200) of the present disclosure is illustrated. As shown, the device 200 may include an earmuff body 202 that defines an exterior surface 204 and an interior cavity 214 opposite the exterior surface 204. The interior cavity 214 may be configured to, as shown in FIGS. 2B-2C, receive an ear 104 of a user 102 therein. The interior cavity 214 may define any recess, alcove, depression, or other concave feature that may receive the ear 104 of the user 102 therein. As shown, the interior cavity 214 may be configured to substantially encircle and/or enclose the user's ear 104 and may employ a sealing membrane 206 to that end. For example, a sealing membrane 206 may be disposed at a juncture between the interior cavity 214 and the exterior surface 204 (e.g., disposed along an exterior edge of the interior cavity 214 at the exterior surface 204). The sealing membrane 206 may comprise any material, dimension, shape, etc. configured to substantially seal the interior cavity 214 from an external environment in an instance in which the hearing safety device 200 is worn by the user 102. A shown in FIG. 2C, the sealing membrane may be configured to be placed in contact with the user's 102 face, head, etc. in order to create a seal around the user's ear 104. Additionally, the interior cavity 214 may be dimensioned (e.g., sized and shaped) to accommodate ears of any shape, size, orientation, etc. based upon the intended application of the device 200.

The exterior surface 204 may be similarly dimensioned (e.g., sized and shaped) based upon the associated dimensions of the interior cavity 214 and may be formed of, for example, a hard thermoplastic or metal material in order to protect the components of the device 200 supported therein. The body 202 defining the interior cavity 214 and the exterior surface 204 may be formed of any acoustic or sound dampening material as would be evident based upon the intended application of the device 200. For example, the body 202 (e.g., the material extending between the interior cavity 214 and the exterior surface 204) may be formed of an acoustic foam configured to attenuate sound waves by increasing the air resistance experienced by sound waves received by the acoustic foam so as to reduce the amplitude (e.g., intensity or level) of these sound waves. By way of a nonlimiting example, the earmuff body 202 may be configured to reduce sound intensity or level (e.g., measured in decibels (dBs)) by approximately 20-35 dB. Such a reduction is often referred to as a noise reduction rating (NRR). The National Institute for Occupational Safety and Health (NIOSH) ratings, for example, recommend that occupational noise exposure be limited at 85 dBs (e.g., an 8-hour time-weighted average of 85 dBA).

Figure 2C:
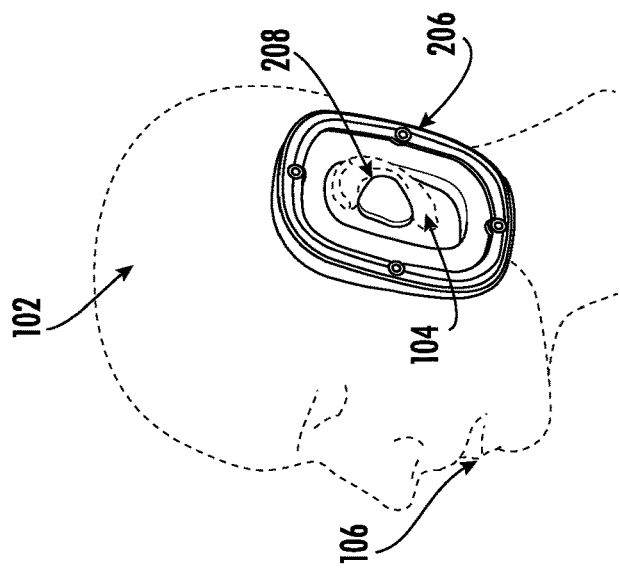
FIGS. 2A-2C illustrate portions of an example hearing safety device in accordance with some example embodiments described herein.
Figure 2B:
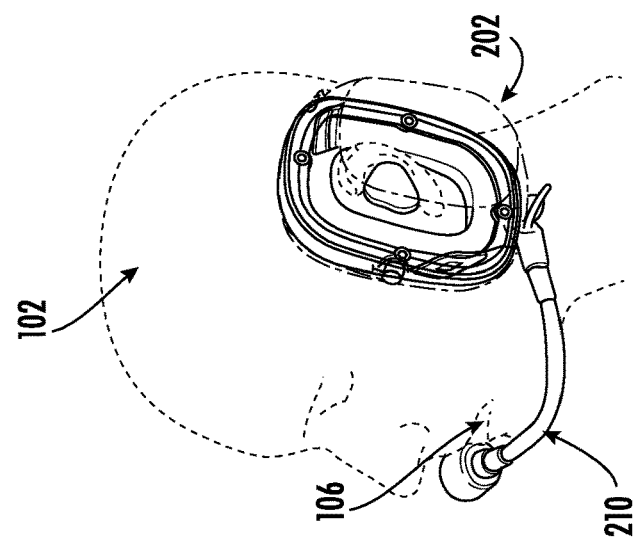
Figure 2A:
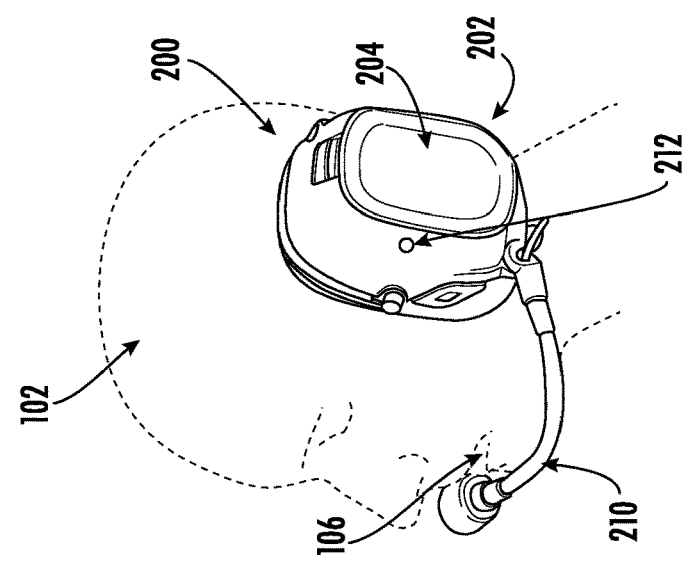

As shown in FIGS. 2A-2B, the hearing safety device 200 may, in some embodiments, further include a microphone 210 attached to the exterior surface 204 of the earmuff body 202. The microphone 210 may be configured to be disposed proximate the user's mouth 106 in an instance in which the hearing safety device 200 is worn by the user 102. As described above, the device 200 may be configured for use in environments in which the user 102 communicates with other users. As such, the microphone 210 may be, in some embodiments, configured to receive a user inputted communication that may be, via assistance of the controller described hereafter, transmitted to one or more other devices, systems, computing entities, or the like communicably coupled with the device 200.

As described above, the use of an earmuff or headphone alone is often insufficient to provide adequate hearing protection. For example, many industries expose users to sound intensities or levels that exceed 140 dB (e.g., aircraft engine noise, gunshots, drilling equipment, etc.) such that a reduction of only 35 dB provided by an earmuff alone fails to comply with NIOSH ratings. As such, the hearing safety device 200 of the present disclosure may further leverage an ear lid 208 attached to an interior surface 218 of the interior cavity 214. The ear lid 208 may project into the interior cavity 214 from the interior surface 218 so as to engage a user 102 when the hearing safety device 200 is worn by a user. Said differently, the ear lid 208 may be affixed to the interior surface 218 so as to provide an integral solution in which further attenuation may be provided without a separate, distinct device (e.g., additional ear plugs). The attachment of the ear lid 208 with the surface 218 of the interior cavity 214 may be such that the ear lid 208 may move as described hereafter.

The ear lid 208 may define a sealing surface 209 configured to substantially seal an ear canal of the user 102 when the hearing safety device 200 is worn by the user 102. The sealing surface 209 may be configured to be disposed at the user's ear 104 and abut the user's ear canal. For example, the sealing surface 209 may be configured to, in some embodiments, abut the user's ear 104 so as to contact at least the tragus of the user's ear while covering the concha and intertragal notch of the user's ear 104. As described above with reference to traditional designs, the use of conventional ear plugs requires that these devices be properly inserted within a user's ear canal to be effective. In practice, however, ear plugs are often misused by users in that they aren't properly secured at an appropriate location within a user's ear canal due to user error and are often uncomfortable to the user resulting in infrequent use. The sealing surface 209 of the hearing safety device 200, however, is configured to prevent entry of the ear lid 208 into the ear canal of the user 102 when the hearing safety device 200 is worn by the user 102. For example, the sealing surface 209 may be dimensioned (e.g., sized and shaped) so as to cover the ear canal of the user 102 without entering the ear canal. The present disclosure contemplates that the shape, contours, orientation, etc. of the sealing surface 209 may be, in some embodiments, based upon the corresponding shapes, contours, orientation, etc. of the user's ear 104 received by the device 200.

Figure 3:
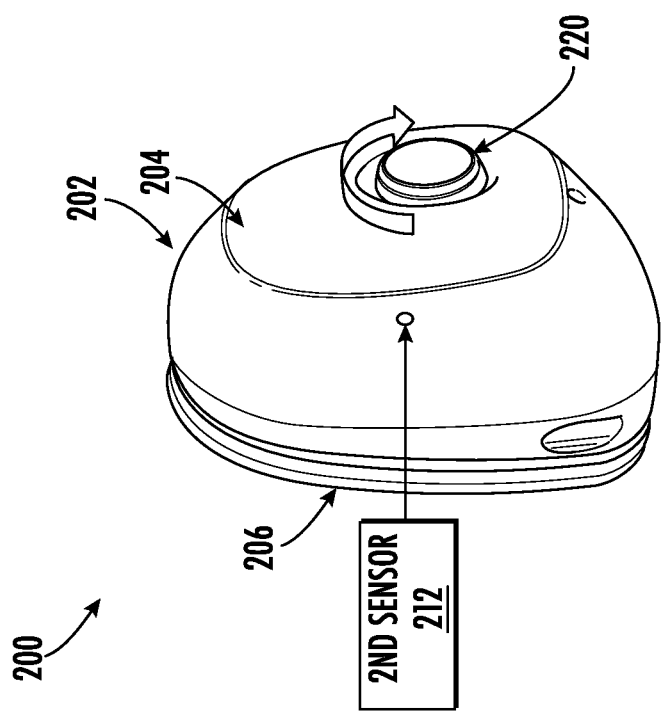
FIG. 3 illustrates an exterior perspective view of the example hearing safety device of FIGS. 2A-2C in a stored position in accordance with some example embodiments described herein.

In order to provide adjustability of attenuation as indicated above, the hearing safety device 200 may leverage an adjustment mechanism 216 operably attached to the ear lid 208 and configured to move the ear lid 208 relative the interior cavity 214 of the earmuff body 202. In some embodiments, the adjustment mechanism 216 may comprise a spring configured to urge the ear lid 208 toward the ear canal of the user 102 when the device 200 is worn by the user 102. For example, the user 102 may place the earmuff body 202 proximate the user's ear 104 such that the user's ear 104 is received by the interior cavity 214 of the body 202 as detailed above. The user's ear 104 may contact the sealing surface 209 of the ear lid 208 and compress the spring (e.g., an example adjustment mechanism 216) such that the spring imparts a force on the ear lid 208 and the user 102. In some embodiments, as shown in FIG. 3, the adjustment mechanism 216 may further include an adjustment input device 220 operably attached to the example spring and configured to modify the tension in the spring so as to modify the force applied to the ear lid 208 and the user 102. By way of example, the adjustment input device 220 may comprise a rotary knob defined by the exterior surface 204 of the earmuff body 202 that, when rotated, increases or reduces the tension applied to the spring's attachment to the body 202 resulting in an increased or decreased, respectively, force applied to the ear lid 208. Although described herein with reference to a rotary knob as an example adjustment mechanism 220, the present disclosure contemplates that any adjustment mechanism 220 (e.g., button, switch, etc.) may be used and may be positioned at any location on or separate from the body 202.

Figure 5:
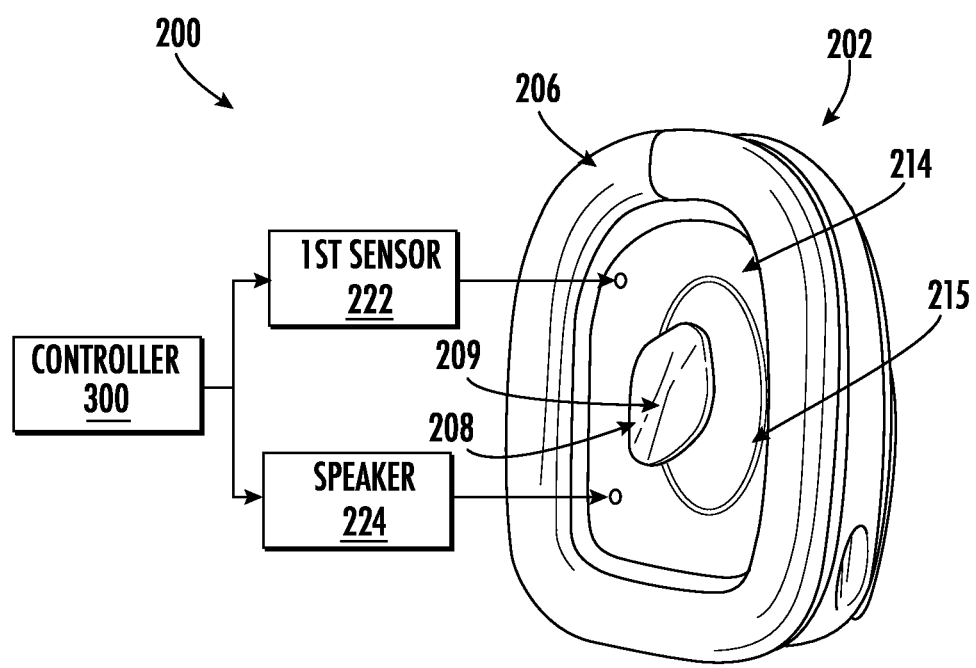
FIG. 5 illustrates the interior perspective view of FIG. 4 with an associated controller in accordance with some example embodiments described herein.

Although described above with reference to an adjustment mechanism 216 that includes a spring, the adjustment mechanism 216 may, additionally or alternatively, employ other devices for causing movement of the ear lid 208 relative to the interior cavity 214. By way of example, the adjustment mechanism 216 may employ one or more motors, cams, linkages, shafts, gears, or the like configured to cause movement of the ear lid 208. By way of a nonlimiting example, the adjustment mechanism 216 may, in some embodiments, include a motor (not shown) housed by the body 202 that is operably connected with an adjustment input device 220 for controlling operation of the motor (not shown). The example motor may be further coupled with one end of a shaft (not shown) that is coupled via an opposing end of the shaft with the ear lid 208 such that output of the motor (not shown) causes the shaft (not shown) to rotate to extend or retract the ear lid 208 so as to modify the force applied to the ear lid 208 and, by association, the user 102. As shown in FIG. 5, the adjustment mechanism 216 may, for example, be covered by a protective layer 215 configured to shield the adjustment mechanism 216. For example the protective layer 215 may comprise a foam material to further increase the comfort associated with the device 200.

In order to determine an adjustment to the ear lid 208, via the adjustment mechanism 216, the hearing safety device 200 may include one or more sensors. As shown in FIGS. 2A and 3, the device 200 may include a second sensor 212 operably coupled with an exterior environment of the hearing safety device 200 and configured to generate second sensor data indicative of a sound intensity of the exterior environment. By way of example, the second sensor 212 may be supported by the body 202 and define an opening in the exterior surface 204 so as to be in fluid communication with the external environment of the device 200. In doing so, the second sensor 212 may receive sound waves from the ambient or external environment and generate second sensor data indicative of the sound level or intensity (e.g., in decibels) of the ambient or external environment. The second sensor 212 may comprise any sensor device configured to determine sound level or intensity, such as a sound level meter, sound pressure level meter (SPL), noise dosemeter, or the like.

Figure 4:
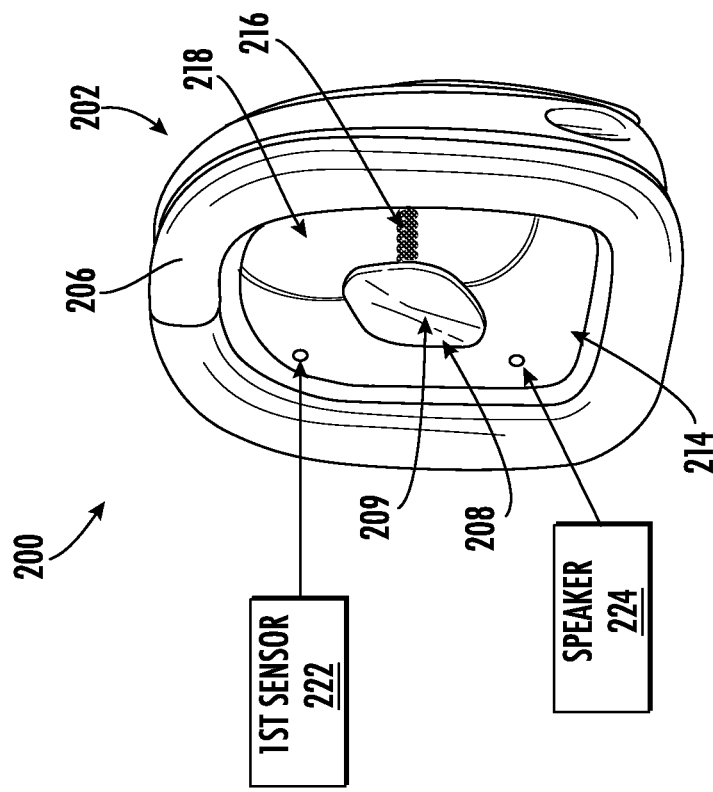
FIG. 4 illustrates an interior perspective view of the example hearing safety device of FIGS. 2A-2C in a stored position in accordance with some example embodiments described herein.

As shown in FIGS. 4 and 5, the device 200 may also include a first sensor 222 operably coupled with the interior cavity 214 and configured to generate first sensor data indicative of a sound intensity within the interior cavity 214. By way of example, the first sensor 222 may be supported by the body 202 and define an opening in the interior cavity 214 so as to be in fluid communication with the internal environment of the device 200 (e.g., the interior of the body 202). In doing so, the first sensor 222 may receive sound waves within the body 202 and generate first sensor data indicative of the sound level or intensity (e.g., in decibels) of the interior of the body 202. The first sensor 222 may similarly comprise any sensor device configured to determine sound level or intensity, such as a sound level meter, sound pressure level meter (SPL), noise dosemeter, or the like.

In order to provide communication transmissions to the user 102, the hearing safety device 200 may further include a speaker 224 operably coupled with the interior cavity 214 of the earmuff body 202 and configured to output sound as shown in FIGS. 4-5. As described above, the device 200 may be used in environments in which communications from (e.g. via the microphone 210) and communications to (e.g., via the speaker 224) are desired. For example, the hearing safety device 200 may be formed as part of a network of hearing safety devices such that users of these devices may communicate with one another via said network. By way of an additional example, the hearing safety device 200 may be communicably coupled with a central device, system, user, or the like so as to receive instructions from said central device (e.g., a tower controller at an airport transmitting instructions to a user wearing the device 200). The speaker 224 may define an opening in the surface 218 of the interior cavity 214 so as to be in fluid communication with the interior of the body 202. The speaker 224 may include any device configured to generate sound, such as an electroacoustic transducer.

Example Computing Device

As shown in FIG. 4, the hearing safety device 200 may include a controller 300 that is operably or communicably coupled with the adjustment mechanism 216, the first sensor 222, the second sensor 212, and/or the speaker 224. In some instances, the body 202 may comprise or otherwise support the controller 300, in whole or in part, such that the hearing safety device 200 is formed as a single, integrated device. In other embodiments, the controller 300 may be operably coupled with the adjustment mechanism 216, the first sensor 222, the second sensor 212, and/or the speaker 224 via a network (not shown).

The controller 300 may include circuitry, networked processors, or the like configured to perform some or all of the apparatus-based processes described herein, and may be any suitable processing device and/or network server. In this regard, the controller 300 may be embodied by any of a variety of devices. For example, the controller 300 may be configured to receive/transmit data (e.g., sound transmission data, sensor data, etc.) and may include any of a variety of fixed terminals, such as a server, desktop, or kiosk, or it may comprise any of a variety of mobile terminals, such as a portable digital assistant (PDA), mobile telephone, smartphone, laptop computer, tablet computer, or in some embodiments, a peripheral device that connects to one or more fixed or mobile terminals. Example embodiments contemplated herein may have various form factors and designs but will nevertheless include at least the components illustrated in FIG. 6 and described in connection therewith. The controller 300 may, in some embodiments, comprise several servers or computing devices performing interconnected and/or distributed functions. Despite the many arrangements contemplated herein, the controller 300 is shown and described herein as a single computing device to avoid unnecessarily overcomplicating the disclosure.

As described above, in some instances, the computing device may be operably coupled with the adjustment mechanism 216, the first sensor 222, the second sensor 212, and/or the speaker 224 via a network. By way of example, the controller 300 may be associated with a central management system or central computing device configured to, in whole or in part, transmit instructions to or control operation of a plurality of devices. In such an embodiment, the network may include one or more wired and/or wireless communication networks including, for example, a wired or wireless local area network (LAN), personal area network (PAN), metropolitan area network (MAN), wide area network (WAN), or the like, as well as any hardware, software and/or firmware for implementing the one or more networks (e.g., network routers, switches, hubs, etc.). For example, the network may include a cellular telephone, mobile broadband, long term evolution (LTE), GSM/EDGE, UMTS/HSPA, IEEE 802.11, IEEE 802.16, IEEE 802.20, Wi-Fi, dial-up, and/or WiMAX network. Furthermore, the network may include a public network, such as the Internet, a private network, such as an intranet, or combinations thereof, and may utilize a variety of networking protocols now available or later developed including, but not limited to TCP/IP based networking protocols. In some embodiments, the network may refer to a collection of wired connections such that adjustment mechanism 216, the first sensor 222, the second sensor 212, speaker 224, and/or the controller 300 may be physically connected, via one or more networking cables or the like.

Figure 6:
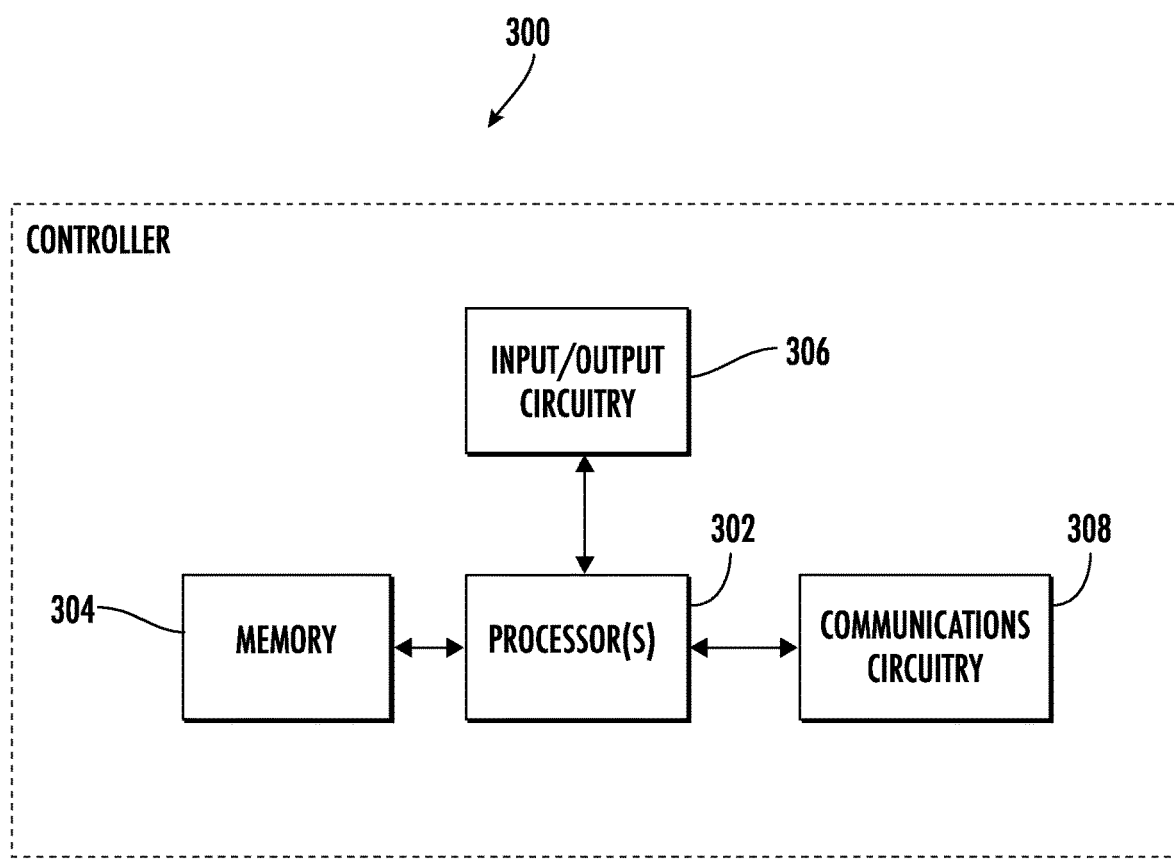
FIG. 6 illustrates a schematic block diagram of an example controller that may perform various operations in accordance with some example embodiments described herein.

As illustrated in FIG. 6, the controller 300 may include a processor 302, a memory 304, input/output circuitry 306, and communications circuitry 308. The controller 300 may be configured to execute the operations described below in connection with FIGS. 7-8. Although components 302-308 are described in some cases using functional language, it should be understood that the particular implementations necessarily include the use of particular hardware. It should also be understood that certain of these components 302-308 may include similar or common hardware. For example, two sets of circuitry may both leverage use of the same processor 302, memory 304, communications circuitry 308, or the like to perform their associated functions, such that duplicate hardware is not required for each set of circuitry. The use of the term "circuitry" as used herein includes particular hardware configured to perform the functions associated with respective circuitry described herein. As described in the example above, in some embodiments, various elements or components of the circuitry of the controller 300 may be housed within components of the device 200. It will be understood in this regard that some of the components described in connection with the controller 300 may be housed within one or more of the devices of FIGS. 1-5, while other components are housed within another of these devices, or by yet another device not expressly illustrated in FIGS. 1-5.

Of course, while the term "circuitry" should be understood broadly to include hardware, in some embodiments, the term "circuitry" may also include software for configuring the hardware. For example, although "circuitry" may include processing circuitry, storage media, network interfaces, input/output devices, and the like, other elements of the controller 300 may provide or supplement the functionality of particular circuitry.

In some embodiments, the processor 302 (and/or co-processor or any other processing circuitry assisting or otherwise associated with the processor) may be in communication with the memory 304 via a bus for passing information among components of the controller 300. The memory 304 may be non-transitory and may include, for example, one or more volatile and/or non-volatile memories. In other words, for example, the memory may be an electronic storage device (e.g., a non-transitory computer readable storage medium). The memory 304 may be configured to store information, data, content, applications, instructions, or the like, for enabling the controller 300 to carry out various functions in accordance with example embodiments of the present disclosure.

The processor 302 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the computing device, and/or remote or "cloud" processors.

In an example embodiment, the processor 302 may be configured to execute instructions stored in the memory 304 or otherwise accessible to the processor 302. Alternatively or additionally, the processor 302 may be configured to execute hard-coded functionality. As such, whether configured by hardware or by a combination of hardware with software, the processor 302 may represent an entity (e.g., physically embodied in circuitry) capable of performing operations according to an embodiment of the present disclosure while configured accordingly. Alternatively, as another example, when the processor 302 is embodied as an executor of software instructions, the instructions may specifically configure the processor 302 to perform the algorithms and/or operations described herein when the instructions are executed.

The controller 300 further includes input/output circuitry 306 that may, in turn, be in communication with processor 302 to provide output to a user and to receive input from a user, user device, or another source. In this regard, the input/output circuitry 306 may comprise a display that may be manipulated by a mobile application. In some embodiments, the input/output circuitry 306 may also include additional functionality including a keyboard, a mouse, a joystick, a touch screen, touch areas, soft keys, a microphone, a speaker, or other input/output mechanisms. The processor 302 and/or user interface circuitry comprising the processor 302 may be configured to control one or more functions of a display through computer program instructions (e.g., software and/or firmware) stored on a memory accessible to the processor (e.g., memory 304, and/or the like).

The communications circuitry 308 may be any means such as a device or circuitry embodied in either hardware or a combination of hardware and software that is configured to receive and/or transmit data from/to a network and/or any other device, circuitry, or module in communication with the controller 300. In this regard, the communications circuitry 308 may include, for example, a network interface for enabling communications with a wired or wireless communication network. For example, the communications circuitry 308 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s). These signals may be transmitted by the controller 300 using any of a number of wireless personal area network (PAN) technologies, such as Bluetooth® v1.0 through v3.0, Bluetooth Low Energy (BLE), infrared wireless (e.g., IrDA), ultra-wideband (UWB), induction wireless transmission, or the like. In addition, it should be understood that these signals may be transmitted using Wi-Fi, Near Field Communications (NFC), Worldwide Interoperability for Microwave Access (WiMAX) or other proximity-based communications protocols.

In addition, computer program instructions and/or other type of code may be loaded onto a computer, processor or other programmable circuitry to produce a machine, such that the computer, processor other programmable circuitry that execute the code on the machine create the means for implementing the various functions, including those described in connection with the components of controller 300.

As described above and as will be appreciated based on this disclosure, embodiments of the present disclosure may be configured as apparatuses, systems, methods, and the like. Accordingly, embodiments may comprise various means including entirely of hardware or any combination of software with hardware. Furthermore, embodiments may take the form of a computer program product comprising instructions stored on at least one non-transitory computer-readable storage medium (e.g., computer software stored on a hardware device). Any suitable computer-readable storage medium may be utilized including non-transitory hard disks, CD-ROMs, flash memory, optical storage devices, or magnetic storage devices.

Example Operations

Figure 7:
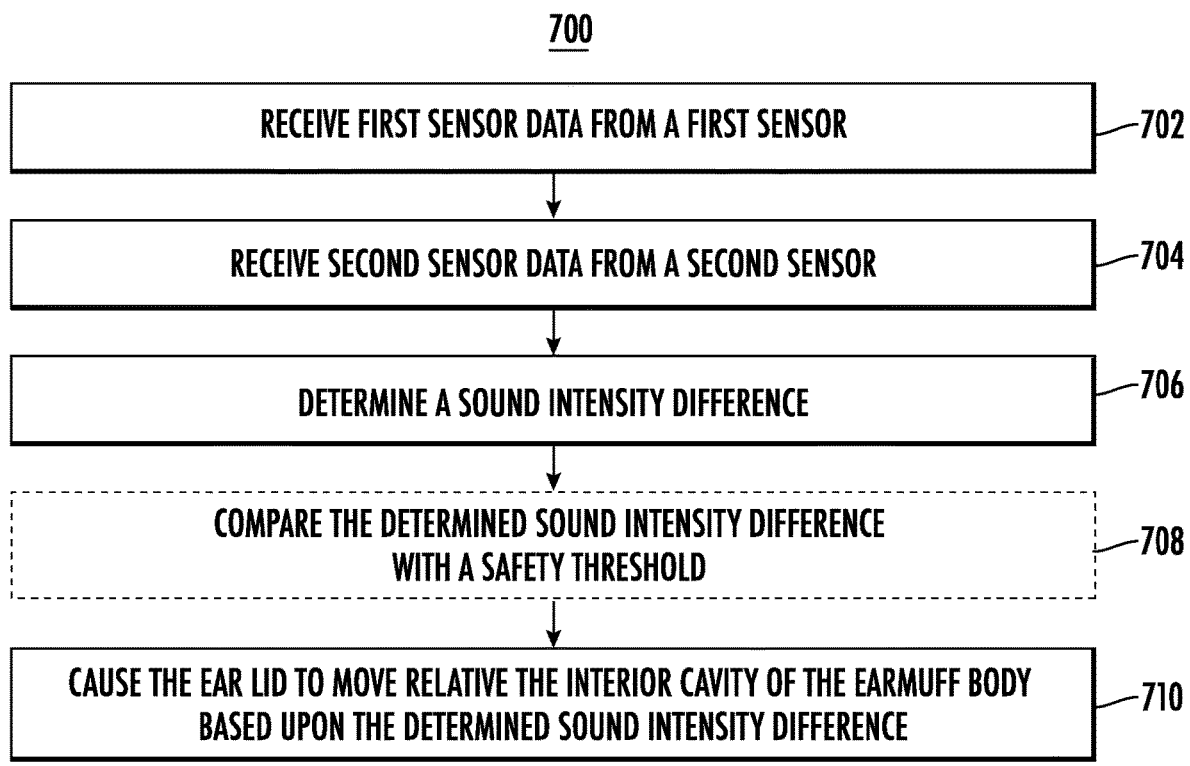
FIG. 7 illustrates an example flowchart for sound intensity determinations in accordance with some example embodiments described herein.

FIG. 7 illustrates a flowchart containing a series of operations for sound intensity determination (e.g., method 700). The operations illustrated in FIG. 7 may, for example, be performed by, with the assistance of, and/or under the control of an apparatus (e.g., controller 300), as described above. In this regard, performance of the operations may invoke one or more of processor 302, memory 304, input/output circuitry 306, and/or communications circuitry 308.

As shown in operation 702, the apparatus (e.g., controller 300) includes means, such as processor 302, communications circuitry 308, or the like, for receiving first sensor data from a first sensor. As described above, the hearing safety device may include a first sensor operably coupled with the interior cavity and configured to generate first sensor data indicative of a sound intensity within the interior cavity. By way of example, the first sensor may be supported by the body and define an opening in the interior cavity so as to be in fluid communication with the internal environment of the device (e.g., the interior of the body). In doing so, the first sensor may receive sound waves within the body and generate first sensor data indicative of the sound level or intensity (e.g., in decibels) of the interior of the body. The first sensor may comprise any sensor device configured to determine sound level or intensity, such as a sound level meter, sound pressure level meter (SPL), noise dosemeter, or the like. The controller 300 may receive the first sensor data from the first sensor periodically, intermittently, in response to a request for first sensor data, or the like.

As shown in operation 704, the apparatus (e.g., controller 300) includes means, such as processor 302, communications circuitry 308, or the like, for receiving second sensor data from a second sensor. As described above, the hearing safety device may include a second sensor operably coupled with an exterior environment of the hearing safety device and configured to generate second sensor data indicative of a sound intensity of the exterior environment. By way of example, the second sensor may be supported by the body and define an opening in the exterior surface so as to be in fluid communication with the external environment of the device. In doing so, the second sensor may receive sound waves from the ambient or external environment and generate second sensor data indicative of the sound level or intensity (e.g., in decibels) of the ambient or external environment. The second sensor may also comprise any sensor device configured to determine sound level or intensity, such as a sound level meter, sound pressure level meter (SPL), noise dosemeter, or the like. The controller 300 may receive the second sensor data from the second sensor periodically, intermittently, in response to a request for second sensor data, or the like.

Thereafter, as shown in operation 706, the apparatus (e.g., controller 300) includes means, such as processor 302 or the like, for determining a sound intensity difference between the sound intensity within the interior cavity and the sound intensity of the exterior environment. As described above, the second sensor data may be indicative of a sound intensity of the exterior environment and the first sensor data may be indicative of a sound intensity within the interior cavity. At operation 706, the processor may determine the mathematical difference between these intensity values to determine the effectiveness (e.g., sound attenuation provided) of the earmuff body so as to determine the amount of attenuation needed by the ear lid. By way of example, the second sensor data generated by the second sensor may indicate a sound intensity of the external environment of the device as approximately 120 dB. The first sensor data generated by the first sensor may indicate a sound intensity of the interior cavity of the device as approximately 90 dB. The determined sound intensity difference for such an example may refer to a value of 30 dB (e.g., that the sound attenuation or NRR for the earmuff body 202 is 30 dB).

In some embodiments, as shown in operation 708, the apparatus (e.g., controller 300) includes means, such as processor 302 or the like, for comparing the determined sound intensity difference with a safety threshold. As described above, various safety regulation, rules, or the like may exist that define maximum sound intensity exposure levels. By way of example, the safety regulation may refer to the NIOSH occupational noise exposure recommended limit of 85 dB (e.g., an 8-hour time-weighted average of 85 dBA). In such an example embodiment, the comparison at operation 708 may refer to a comparison between the 90 dB determined sound intensity difference and the 85 dB safety threshold. In an instance in which the determined sound intensity difference exceeds the safety threshold, for example, the controller 300 may determine that further attenuation is required, and cause movement of the ear lid as described hereafter (e.g., moving the ear lid to seal the user's ear canal). Additionally or alternatively, the determined sound intensity difference may be determined to be, for example 75 dB such that a comparison between the determined sound intensity difference and the above safety threshold of 85 dB indicates that no further attenuation is necessary (e.g., the sound intensity within the interior of the earmuff body is below the maximum safe sound intensity value.) In such an example, the causing of movement of the ear lid described hereafter may instead refer to disengaging the ear lid from the user's ear canal to improve hearing of the user.

Thereafter, as shown in operation 710, the apparatus (e.g., controller 300) includes means, such as processor 302, communications circuitry 308, or the like, for causing the ear lid to move relative the interior cavity of the earmuff body based upon the determined sound intensity difference. By way of continued example, in an instance in which the determined sound intensity difference indicates that further attenuation is required to, for example, satisfy an associated safety threshold, the controller 300 may transmit instructions to the adjustment mechanism causing the ear lid to move into a position that substantially seals the user's ear canal as described above. In some embodiments this movement may refer to an adjustment in the tension on the spring (e.g., a feature of an example adjustment mechanism) so as to increase the force on the ear lid and the user. In an instance in which the determined sound intensity difference indicates that further attenuation is not required to, for example, satisfy an associated safety threshold, the controller 300 may transmit instructions to the adjustment mechanism causing the ear lid to move into a position that substantially opens the user's ear canal as described above. In some embodiments this movement may refer to an adjustment in the tension on the spring (e.g., a feature of an example adjustment mechanism) so as to reduce the force on the ear lid and the user. In some embodiments, the controller 300 may be configured to iteratively receive sensor data from the first sensor and the second sensor and iteratively determine a sound intensity difference so as to dynamically adjust the attenuation provided by the hearing safety device in real or substantially real time. In other words, the embodiments described herein may operate to determine changes in the sound level or intensity of an external environment and dynamically adjust the position of the ear lid to ensure proper sound attenuation.

Figure 8:
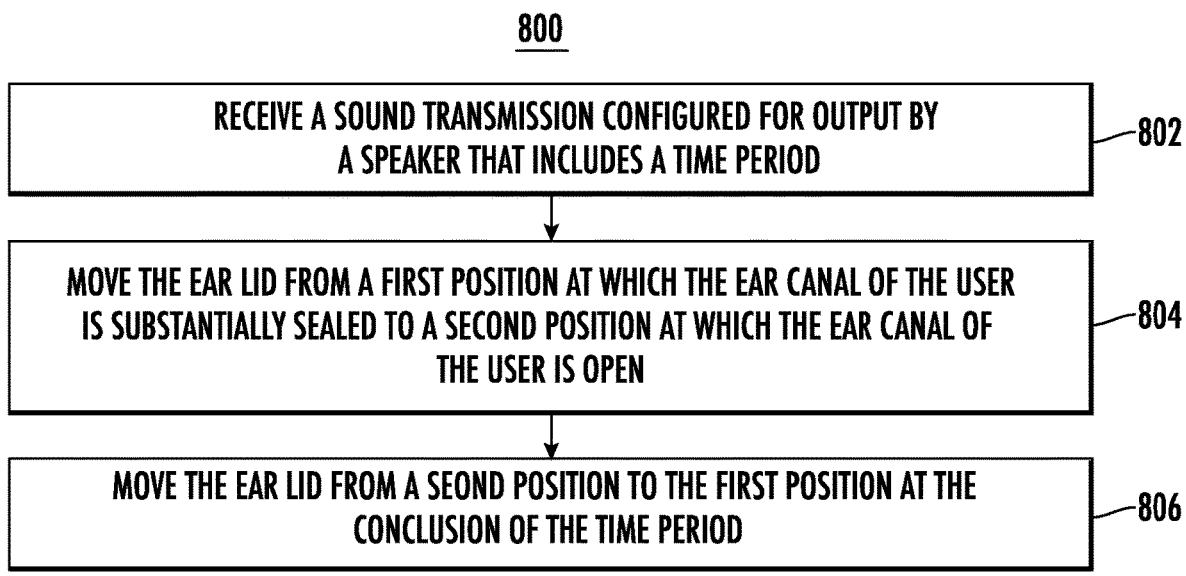
FIG. 8 illustrates an example flowchart for speaker operations in accordance with some example embodiments described herein.

FIG. 8 illustrates a flowchart containing a series of operations for speaker operations (e.g., method 800). The operations illustrated in FIG. 8 may, for example, be performed by, with the assistance of, and/or under the control of an apparatus (e.g., controller 300), as described above. In this regard, performance of the operations may invoke one or more of processor 302, memory 304, input/output circuitry 306, and/or communications circuitry 308.

As shown in operation 802, the apparatus (e.g., controller 300) includes means, such as processor 302, communications circuitry 308, or the like, for receiving a sound transmission configured for output by the speaker. In some embodiments, the sound transmission may define a time period during which the sound transmission is output by the speaker. As described above, the hearing safety device of the present disclosure may be used in environments in which communication with the device is desired. In traditional systems that rely upon earmuffs in conjunction with ear plugs within a user's ear canal, a user is often incapable of hearing communications transmitted to the device. As such, the embodiments of the present disclosure may provide a variable ear lid that may, in response to a communication transmission, move the ear lid to allow for the transmission to be properly received by the user. The transmission received at operation 802 may be received by the controller 300 and configured to output by the speaker within the interior cavity as described above.

Thereafter, as shown in operation 804, the apparatus (e.g., controller 300) includes means, such as processor 302, communications circuitry 308, or the like, for moving, via the adjustment mechanism, the ear lid from a first position at which the ear canal of the user is substantially sealed to a second position at which the ear canal of the user is open. By way of example, the controller 300 may receive a signal transmission as described above that is associated with a time period during which sound is outputted by the speaker (e.g., a beginning time and an end time or duration of the signal transmission). The controller may, prior to the beginning time of the output of the signal transmission, transmit an instruction to the adjustment mechanism to move the ear lid from a first position at which the ear canal of the user is substantially sealed to a second position at which the ear canal of the user is open. In doing so, the attenuation provided by the ear lid may be momentarily reduced, but the user may be able to properly receive (e.g., hear) the contents of the signal transmission.

Thereafter, as shown in operation 806, the apparatus (e.g., controller 300) includes means, such as processor 302, communications circuitry 308, or the like, for moving, via the adjustment mechanism, the ear lid from the second position to the first position at the conclusion of the time period. By way of continued example, the signal transmission may include an end at which output of the signal transmission by the speaker halts. The controller may, following completion of output of the signal transmission, transmit an instruction to the adjustment mechanism to move the ear lid from the second position at which the ear canal of the user is substantially open to the first position at which the ear canal of the user is substantially sealed. In doing so, the controller may operate to return the user into proper compliance (e.g., with proper attenuation provided by the ear lid) after the user properly receives (e.g., hears) the contents of the signal transmission.

FIGS. 7 and 8 thus illustrate flowcharts describing the operation of apparatuses, methods, and computer program products according to example embodiments contemplated herein. It will be understood that each flowchart block, and combinations of flowchart blocks, may be implemented by various means, such as hardware, firmware, processor, circuitry, and/or other devices associated with execution of software including one or more computer program instructions. For example, one or more of the operations described above may be implemented by an apparatus executing computer program instructions. In this regard, the computer program instructions may be stored by a memory 304 of the controller 300 and executed by a processor 302 of the controller 300. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the functions specified in the flowchart blocks. The computer program instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the flowchart blocks.

The flowchart blocks support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware with computer instructions.

The invention claimed is:

1. A hearing safety device configured to be worn by a user, the hearing safety device comprising:
    an earmuff body, the earmuff body defining:
        an interior cavity configured to receive the user's ear therein when worn by the user; and
        an exterior surface opposite the interior cavity;
    an ear lid attached to a surface of the interior cavity, wherein the ear lid projects into the interior cavity from the surface of the interior cavity, the ear lid defining a sealing surface configured to substantially seal an ear canal of the user's ear when the hearing safety device is worn by the user;
    a first sensor operably coupled with the interior cavity and configured to generate first sensor data indicative of a sound intensity within the interior cavity;
    a second sensor operably coupled with an exterior environment of the hearing safety device and configured to generate second sensor data indicative of a sound intensity of the exterior environment; and
    an adjustment mechanism operably attached to the ear lid and configured to move the ear lid relative to the interior cavity of the earmuff body based on a sound intensity difference, wherein the sound intensity difference is a difference between the sound intensity within the interior cavity and the sound intensity of the exterior environment.

2. The hearing safety device according to claim 1, wherein the sealing surface is further configured to prevent entry of the ear lid into the ear canal of the user when the hearing safety device is worn by the user.

3. The hearing safety device according to claim 2, wherein a shape of the sealing surface corresponds to a shape of the user's ear.

4. The hearing safety device according to claim 2, wherein the sealing surface is configured to contact the tragus of the user's ear and cover the concha and intertragal notch of the user's ear.

5. The hearing safety device according to claim 1, wherein the sealing surface is further dimensioned to cover the ear canal of the user without entering the ear canal.

6. The hearing safety device according to claim 1, wherein the adjustment mechanism comprises a spring configured to urge the ear lid toward the ear canal of the user when the hearing safety device is worn by the user.

7. The hearing safety device according to claim 6, wherein the adjustment mechanism further comprises an adjustment input device operably attached to the spring and configured to modify a tension in the spring so as to modify a force applied to the ear lid and the user.

8. The hearing safety device according to claim 7, wherein the adjustment input device comprises a rotary knob defined by the exterior surface of the earmuff body.

9. The hearing safety device according to claim 1, further comprising a sealing membrane disposed at a juncture between the interior cavity and the exterior surface, the sealing membrane configured to substantially seal the interior cavity from an external environment in an instance in which the hearing safety device is worn by the user.

10. The hearing safety device according to claim 1, further comprising a microphone attached to the exterior surface of the earmuff body, the microphone configured to be disposed proximate the user's mouth in an instance in which the hearing safety device is worn by the user.

11. The hearing safety device according to claim 1, wherein the adjustment mechanism is configured to move the ear lid relative to the interior cavity of the earmuff body based on the sound intensity difference satisfying a safety threshold.

12. The hearing safety device according to claim 1, further comprising a speaker operably coupled with the interior cavity of the earmuff body and configured to output sound, and further comprising a controller operably coupled with the speaker, the controller configured to:
    receive a sound transmission configured for output by the speaker; and
    cause, via the adjustment mechanism, the ear lid to move relative to the interior cavity of the earmuff body in response to the sound transmission.

13. The hearing safety device according to claim 12, wherein the sound transmission defines a time period during which the sound transmission is output by the speaker, wherein the controller further configured to:
    move, via the adjustment mechanism, the ear lid from a first position at which the ear canal of the user is substantially sealed to a second position at which the ear canal of the user is open; and
    move, via the adjustment mechanism, the ear lid from the second position to the first position at a conclusion of the time period.

14. The hearing safety device according to claim 1, wherein the adjustment mechanism comprises a motor and a shaft that is coupled to the motor, wherein the motor is configured to rotate the shaft, and wherein rotation of the shaft causes the ear lid to move.

15. The hearing safety device according to claim 1, further comprising a protective layer that covers the adjustment mechanism, wherein the protective layer comprises a foam material.

16. A method comprising:
receiving first sensor data from a first sensor operably coupled with an interior cavity defined by an earmuff body of a hearing safety device, wherein the first sensor data is indicative of a sound intensity within the interior cavity;
receiving second sensor data from a second sensor operably coupled with an exterior environment of the hearing safety device that is opposite the interior cavity, wherein the second sensor data is indicative of a sound intensity of the exterior environment;
determining a sound intensity difference between the sound intensity within the interior cavity and the sound intensity of the exterior environment; and
causing an ear lid attached to a surface of the interior cavity that projects into the interior cavity from the surface to move relative to the interior cavity to a position that substantially seals an ear canal of the user's ear when the hearing safety device is worn by the user, wherein an adjustment mechanism operably attached to the ear lid is configured to move the ear lid relative to the interior cavity of the earmuff body based on the determined sound intensity difference.

17. The method according to claim 16, wherein determining the sound intensity difference further comprises:
comparing the determined sound intensity difference with a safety threshold; and
causing, via the adjustment mechanism, the ear lid to move in an instance in which the determined sound intensity difference satisfies the safety threshold.

18. The method according to claim 16, further comprising:
receiving a sound transmission configured for output by a speaker operably coupled with the interior cavity of the earmuff body and configured to output sound; and
causing, via the adjustment mechanism, the ear lid to move relative to the interior cavity of the earmuff body in response to the sound transmission.

19. The method according to claim 16, further comprising:
receiving a sound transmission configured for output by a speaker operably coupled with the interior cavity of the earmuff body and configured to output sound, wherein the sound transmission defines a time period during which the sound transmission is output by the speaker;
moving, via the adjustment mechanism, the ear lid from a first position at which the ear canal of the user is substantially sealed to a second position at which the ear canal of the user is open; and
moving, via the adjustment mechanism, the ear lid from the second position to the first position at a conclusion of the time period.

20. A computer program product comprising at least one non-transitory computer-readable storage medium having computer program code thereon that, in execution with at least one processor, configures the computer program product for:
receiving first sensor data from a first sensor operably coupled with an interior cavity defined by an earmuff body of a hearing safety device, wherein the first sensor data is indicative of a sound intensity within the interior cavity;
receiving second sensor data from a second sensor operably coupled with an exterior environment of the hearing safety device that is opposite the interior cavity, wherein the second sensor data is indicative of a sound intensity of the exterior environment;
determining a sound intensity difference between the sound intensity within the interior cavity and the sound intensity of the exterior environment; and
causing an ear lid attached to a surface of the interior cavity that projects into the interior cavity from the surface to move relative to the interior cavity to a position that substantially seals an ear canal of the user's ear when the hearing safety device is worn by the user, wherein an adjustment mechanism operably attached to the ear lid is configured to move the ear lid relative to the interior cavity of the earmuff body based on the determined sound intensity difference.

* * * * *